(12) United States Patent
Mansouri et al.

(10) Patent No.: US 8,560,251 B2
(45) Date of Patent: Oct. 15, 2013

(54) SYSTEM AND METHOD OF INCREASING SAMPLE THROUGHPUT BY ESTIMATION OF A SENSOR ENDPOINT

(75) Inventors: Sohrab Mansouri, Sudbury, MA (US); Jose Maria Cervera, Arlington, MA (US)

(73) Assignee: Instrumentation Laboratory Company, Bedford, MA (US)

( * ) Notice: Subject to any disclaimer, the term of this patent is extended or adjusted under 35 U.S.C. 154(b) by 87 days.

(21) Appl. No.: 13/210,810

(22) Filed: Aug. 16, 2011

(65) Prior Publication Data

US 2013/0046478 A1 Feb. 21, 2013

(51) Int. Cl.
| | |
|---|---|
| *A61B 5/1495* | (2006.01) |
| *G01N 33/50* | (2006.01) |
| *A61B 5/145* | (2006.01) |
| *G01N 27/327* | (2006.01) |
| *C12Q 1/26* | (2006.01) |
| *G01N 35/00* | (2006.01) |
| *C12Q 1/00* | (2006.01) |
| *A61B 5/1486* | (2006.01) |

(52) U.S. Cl.
CPC .............. *A61B 5/1495* (2013.01); *G01N 33/50* (2013.01); *G01N 27/327* (2013.01); *G01N 2035/00702* (2013.01); *G01N 2035/0097* (2013.01); *C12Q 1/002* (2013.01); *C12Q 1/006* (2013.01); *A61B 5/145* (2013.01); *A61B 5/1486* (2013.01)
USPC ................. 702/32; 702/19; 702/22; 600/309; 600/347; 435/14; 435/174

(58) Field of Classification Search
None
See application file for complete search history.

(56) References Cited

U.S. PATENT DOCUMENTS

| | | | |
|---|---|---|---|
| 5,890,489 A * | 4/1999 | Elden ............................ | 128/898 |
| 6,424,847 B1 * | 7/2002 | Mastrototaro et al. ........ | 600/316 |
| 6,615,064 B1 * | 9/2003 | Aldrich ......................... | 600/316 |
| 6,652,720 B1 | 11/2003 | Mansouri et al. | |
| 7,022,219 B2 | 4/2006 | Mansouri et al. | |
| 7,087,149 B1 * | 8/2006 | Muguruma et al. .......... | 205/778 |
| 7,632,672 B2 | 12/2009 | Pamidi et al. | |
| 7,972,280 B2 | 7/2011 | Azer et al. | |
| 8,042,073 B1 | 10/2011 | Nnaji | |
| 8,112,375 B2 | 2/2012 | Pav | |
| 8,226,555 B2 | 7/2012 | Say et al. | |
| 8,231,532 B2 | 7/2012 | Say et al. | |
| 8,231,534 B2 | 7/2012 | Habu et al. | |

(Continued)

OTHER PUBLICATIONS

McDonald, J. H. Handbook of Biological Statistics. (2008). Excerpt of pp. 205-210.*
Motulsky, H. J. PRISM 4 Statistics Guide. (GraphPad Software, Inc., San Diego CA, 2005). 3 excerpted pages, with 2 pages of front matter.*

(Continued)

*Primary Examiner* — Soren Harward
(74) *Attorney, Agent, or Firm* — Burns & Levinson, LLP

(57) ABSTRACT

Technologies for increasing sample throughput by predicting the end point response time of a sensor for the analysis of an analyte in a sample are disclosed. In one aspect, a system includes a sensor that generates data signals associated with the measurement of an analyte within the sample. A processor records appropriate data points corresponding to the signals, converts them to a logarithmic function of time scale, and plots the converted data points. The processor then determines a curve that fits the plotted data points and determines a curve fitting equation for the curve. Once the equation is determined, the processor extrapolates an end point response of the sensor using the equation. A value, such as analyte concentration, is then calculated using the extrapolated end point response.

21 Claims, 4 Drawing Sheets

(56) References Cited

U.S. PATENT DOCUMENTS

| | | | |
|---|---|---|---|
| 2002/0053523 A1 | 5/2002 | Liamos | |
| 2005/0130249 A1* | 6/2005 | Parris et al. | 435/14 |
| 2005/0203360 A1* | 9/2005 | Brauker et al. | 600/345 |
| 2006/0167351 A1* | 7/2006 | Isaacson et al. | 600/323 |
| 2008/0102441 A1 | 5/2008 | Chen | |
| 2008/0114549 A1 | 5/2008 | Schafer et al. | |
| 2008/0215254 A1* | 9/2008 | Leiner et al. | 702/25 |
| 2009/0194432 A1 | 8/2009 | Deng | |
| 2010/0049022 A1 | 2/2010 | Parris et al. | |
| 2010/0168535 A1* | 7/2010 | Robinson et al. | 600/309 |
| 2012/0209566 A1 | 8/2012 | Idiart | |

OTHER PUBLICATIONS

Wang, J. Glucose Biosensors: 40 Years of Advances and Challenges. Electroanalysis 13, 983-988 (2001).*

Ch. 6—Kaohsiung University Prof. Ray-Bing Chen, Regression Analysis: Fall 2008 (Power-point files) pp. 1-33.

Patent Cooperation Treaty, International Search Report (ISR) & Written Opinion of the ISR, International Application No. PCT/US2012/051049, mailed on Nov. 2, 2012; 9 pages.

Looking at Data—Relationships cautions about correlation and regression Available online: https://www.stt.msu.edu/Academics/ClassPages/uploads/FS12/421-1/Lecture_ch2_part4.pdf, 2009.

* cited by examiner

SYSTEM AND METHOD OF INCREASING SAMPLE THROUGHPUT BY ESTIMATION OF A SENSOR ENDPOINT

FIELD OF THE INVENTION

The present invention relates to increasing sample throughput. The present invention is more specifically related to a device, such as an automated clinical analyzer of body fluids, such as blood, and method for increasing sample throughput through the analyzer by predicting the end point response of an electrochemical sensor that responds to the presence of an analyte in a body fluid sample.

BACKGROUND OF THE INVENTION

In a variety of clinical situations, it is important to measure certain chemical characteristics of a patient's blood, such as pH, hematocrit, the ion concentration of calcium, potassium, chloride, sodium, glucose, lactate, creatinine, creatine, urea, partial pressure of O2 and/or CO2, and the like. These situations may arise in a routine visit to the doctor's office, in the surgical suite, intensive care unit, or emergency room. The speed with which the analytical response is obtained is important for determining therapy and therapeutic outcome. A delay in the response time of a sensor slows diagnosis, and, with it, the application of appropriate therapy. Such delays may impact prognosis and clinical outcome.

Electrochemical sensors such as those described in U.S. Pat. Nos. 6,652,720; 7,632,672; 7,022,219; and 7,972,280, the entire disclosure of each of which is incorporated herein by reference, are typically used to provide blood chemistry analysis of a patient's blood.

Conventional microelectrodes generate electrical signals proportional to chemical characteristics of the blood sample. To generate these electrical signals, the sensor systems may combine a chemical or biochemical recognition component, such as an enzyme, with a physical transducer such as a platinum electrode. Traditional chemical or biochemical recognition components selectively interact with an analyte of interest to generate, directly or indirectly, the needed electrical signal through the transducer.

The selectivity of certain biochemical recognition components makes it possible for electrochemical sensors to accurately detect certain biological analytes, even in a complex analyte mixture such as blood. The accuracy and the speed with which these sensors provide a response are important features of automated clinical analyzers.

One of the goals of clinical sample analysis system manufacturers is increasing sample throughput. Recent innovations have focused their attention on reducing the end point response time of a sensor, which is the time the sensor takes to provide an end point response. In conventional clinical analytical systems, once the sensor provides an end point response, the response is provided to a computer, which performs various mathematical operations to convert the end point response to a concentration of an analyte within the body fluid sample. The time taken for the sensor to provide an end point response dictates the time for a sample to be analyzed, which ultimately, determines the sample throughput. Accordingly, there is a need to reduce the time required to analyze a body fluid sample to expedite diagnosis and therapeutic intervention.

SUMMARY OF THE INVENTION

The present invention overcomes the drawbacks of prior art devices and methods and is directed towards technologies for increasing sample, such as body fluid sample, throughput by predicting the end point response time of a sensor for the analysis of an analyte in the sample. According to various embodiments described herein, the present invention describes techniques for extrapolating an end point response of a sensor by determining a curve fitting equation derived from data signals generated by the sensor in response to being exposed to analytes in a sample. In various embodiments, the curve fitting equation will be a second degree logarithmic polynomial having a general form of $s(t)=a(\log(t))^2+b(\log(t))+c$, where a, b, and c are the polynomial coefficients that are determined based on the converted data points, and $s(t)$ is the calculated sensor output at a particular time t.

In one aspect, a system for increasing sample throughput includes a sensor configured to generate a plurality of data signals associated with the measurement of an analyte within the sample. The system further includes a processor that the records data points corresponding to a particular time range within the kinetic region, converts the recorded data points to a logarithmic function of time scale, and plots the converted data points. The processor then determines a curve that fits the plotted data points and determines a curve fitting equation for the curve. Once the curve fitting equation is determined, the processor extrapolates an end point response of the sensor using the curve fitting equation. A value, such as analyte concentration, is then calculated using the extrapolated end point response.

In another aspect, a method for increasing sample throughput includes receiving data signals generated by a sensor in response to being exposed to an analyte within a sample. Once the data signals are received, data points associated with the data signals are recorded. A series of data points corresponding to a portion of a kinetic region time range from the recorded data points are selected and then converted to a logarithmic function of time scale and plotted. A curve that fits the data points is generated and a second degree logarithmic equation for the curve is determined. Once the curve fitting equation is determined, the processor extrapolates an end point response of the sensor using the curve fitting equation. A value, such as analyte concentration, is then calculated using the extrapolated end point response.

In yet another aspect, a computer readable storage medium includes computer executable instructions for receiving data signals generated by a sensor in response to being exposed to an analyte within a sample. Once the data signals are received, data points associated with the data signals are recorded. A series of data points corresponding to a portion of a kinetic region time range from the recorded data points are selected and then converted to a logarithmic function of time scale and plotted. A curve that fits the data points is generated and a second degree logarithmic equation for the curve is determined. Once the curve fitting equation is determined, the processor extrapolates an end point response of the sensor using the curve fitting equation. A value, such as analyte concentration, is then calculated using the extrapolated end point response.

BRIEF DESCRIPTION OF THE DRAWINGS

These embodiments and other aspects of this invention will be readily apparent from the detailed description below and the appended drawings, which are meant to illustrate and not to limit the invention, and in which.

DESCRIPTION

The present invention is directed towards technologies for increasing sample, such as a body fluid sample, throughput in an automated clinical analyzer by predicting the end point response time of a sensor for the analysis of an analyte in the sample. According to various embodiments described herein, the present invention describes techniques for extrapolating an end point response of a sensor by determining a curve fitting equation derived from data signals generated by the sensor in response to being exposed to a sample. In various embodiments, the curve fitting equation will be a second degree logarithmic polynomial having a general form of $s(t)=a(\log(t))^2+b(\log(t))+c$, where a, b, and c are the polynomial coefficients that are determined based on the converted data points, and s(t) is the calculated sensor output at a particular time t. In this way, a sample analysis system may no longer need to wait the entire duration of the sensor end point response time to analyze a sample and provide a determination of the concentration of the analyte measured by the sensor in the sample. Moreover, by reducing the sensor response time, and therefore, the sample exposure time, the sensor recovery time, which is the time the sensor takes to recover is also reduced, allowing for greater throughput.

The present invention will be more completely understood through the following description, which should be read in conjunction with the attached drawings. In this description, like numbers refer to similar elements within various embodiments of the present invention. Within this description, the claimed invention will be explained with respect to embodiments. The skilled artisan will readily appreciate that the methods and systems described herein are merely exemplary and that variations can be made without departing from the spirit and scope of the invention.

Figure 1:
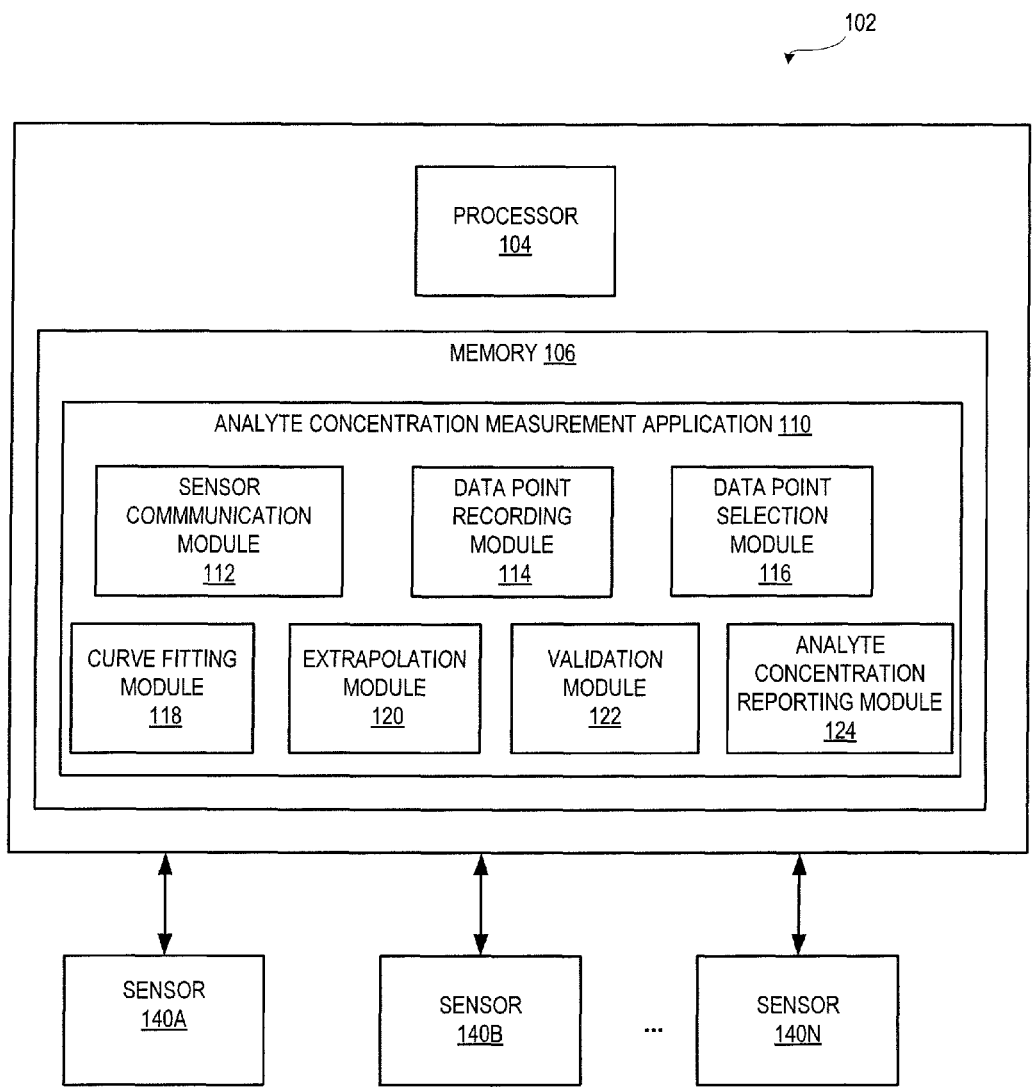
FIG. 1 illustrates an exemplary block diagram of an analyte concentration measurement system according to one embodiment of the invention.

Referring now to the figures, FIG. 1 illustrates a block diagram of an analyte concentration measurement system 102 according to one embodiment of the invention. In particular, an analyte concentration measurement system 102 may include a processor 104, a memory 106, and an analyte concentration measurement application 110 stored in the memory 106. The analyte concentration measurement application 110 may generally be configured to communicate with one or more sensors 140A-N, generally referred to hereinafter as sensors 140. In various embodiments, the sensors 140 may be electrochemical sensors that may generate voltmetric or amperometric signals in response to being exposed to analytes. In various embodiments, a first sensor 140A may be responsive to a first analyte within a sample, a second sensor 140B may be responsive to a second analyte within the sample, and an nth sensor 140N may be responsive to an nth analyte within the sample, and so forth. Further details regarding the sensors 140 are provided below.

The analyte concentration measurement application 110 may include one or more modules configured to perform specific functions or tasks in order to determine the concentration of an analyte within a sample. In various embodiments, the analyte concentration measurement application 110 may include a sensor communication module 112, a data point reporting module 114, a data point selection module 116, a curve fitting module 118, an extrapolation module 120, a validation module 122, and an analyte concentration reporting module 124. It should be appreciated that in various embodiments, the analyte concentration measurement application 110 may include additional modules for performing additional tasks, or may include only some of the modules listed above.

The analyte concentration measurement application 110 may generally be configured to receive data signals generated by a sensor upon being exposed to an analyte within a sample, record data points extracted from the data signals, evaluate the data points on a logarithmic function of time scale, determine a curve that matches the evaluated data points, determine a curve fitting equation that can be utilized to extrapolate an end point response of the sensor, and accurately estimate the concentration of the analyte based on the extrapolated end point response of the sensor.

In various embodiments, the sensor communication module 112 may be configured to receive data signals from the sensors 140. In some embodiments where the sensors may be electrochemical sensors, the data signals may represent an amperometric output that may be measured in Amperes, or a voltmetric output that may be measured in Volts. In various embodiments, these data signals may vary over time, and typically may generate an output value that eventually stabilizes over time. The stabilized output value may typically be the end point response of the sensor. It should be appreciated that any type of sensor that can generate a data output signal in response to being exposed to an analyte may be utilized as a sensor 140.

The data point recording module 114 may be configured to capture and record data points from the generated data signals. The data points may be stored in the memory of the analyte concentration measurement system 102, or at any other storage medium accessible by the analyte concentration measurement application 110. In various embodiments, the data point recording module 114 may record a measurement of the data signal after every nth fixed period of time. The fixed period of time may be predefined by the analyte concentration measurement application 110. It should be appreciated that the fixed period of time may be defined by the technological limitations of existing systems and is not intended to be limited to any particular range. However, in some embodiments, the fixed period of time may range from a millisecond to a few seconds. In alternate embodiments, the data point recording module 114 may record a measurement of the data signal after random or variable periods of time.

The data point selection module 116 may be configured to select pertinent data points from the recorded data points. In various embodiments, the data point selection module 116 may select data points that when plotted on a logarithmic function of time scale, may allow the analyte concentration measurement application to determine a curve that closely fits the selected data points and also results in predicting an end point response of the sensor that is within acceptable limits. In various embodiments, data points that may provide the most accurate results may be selected from a time range that is empirically determined, and may vary depending on characteristics of the sensor and the analyte.

In various embodiments, the data point selection module 116 may select a series of data points corresponding to a kinetic region time range from the recorded data points. The kinetic region time range refers to any time range in which the data points are within the kinetic region of a sensor response.

Typically, the kinetic region occurs from a first time when the sensor is exposed to the analyte, to a second time when the data signals generated by the sensor are not substantially similar to the end point response of the sensor i.e. before the sensor response reaches equilibrium. In other words, once the data signals generated by the sensor become substantially similar to the end point response of the sensor, the data signals are being generated in an equilibrium region. In various embodiments, the data point selection module 116 may select a series of data points corresponding to a portion of a kinetic region time range. In one embodiment, the time range may begin at about fifteen seconds after the sensor is exposed to the analyte. Moreover, the time range may end at about thirty seconds after the sensor is exposed to the analyte. Additional details regarding which data points to select are provided below with respect to FIG. 4.

The curve fitting module 118 may be configured to convert the selected data points to a logarithmic function of time scale such that the converted data points can be evaluated on a logarithmic function of time scale. The curve fitting module may then determine a curve that closely matches the evaluated data points. In various embodiments, the curve fitting module 118 may plot the selected data points on a logarithmic function of time scale, and determine a curve that closely matches or fits the plotted data points. Upon determining the curve, the curve fitting module may determine a curve fitting equation corresponding to the curve. In various embodiments, the equation of the curve fitting equation may be a second degree logarithmic equation having a general form of $s(t)=a(\log(t))^2+b(\log(t))+c$, where a, b, and c are the polynomial coefficients that are determined based on the converted data points, and s(t) is the calculated sensor output at a particular time t. The precise values of a, b, and c, which are determined empirically for each sensor configuration used, depend in part upon the concentration of the analyte, the size of the sample, the temperature, the geometry of the sensor apparatus setup, and other parameters.

The extrapolation module 120 may be configured to extrapolate an end point response of the sensor by solving the curve fitting equation for a time within the equilibrium region of the curve. In various embodiments, the analyte concentration measurement application 102 may utilize empirical methods to determine a time that is within the equilibrium region of the curve, and then store the determined equilibrium region time as a predefined time with which to solve the curve fitting equation.

The validation module 122 may be configured to validate the calculated end point response by determining the coefficient of variation (CV) and the coefficient of determination ($R^2$). The following formulas for determining the coefficient of variation (CV) and the coefficient of determination ($R^2$) are well known in the art and may be used by the validation module 122 to validate the calculated end point response.

$CV=\text{standard deviation}(y_i)/\text{mean}(y_i)$; and $R^2=1-(\text{sum}((y_i-f_i)^2)/(\text{sum}((y_i-\text{mean}(y_i))^2)$;

where $y_i$ and $f_i$ are the observed and calculated values at a specified time, respectively.

It should be appreciated that by way of the present disclosure, the sample exposure time is reduced as the sensor response time is reduced. As a result of the reduced sample exposure time, the sensors, and in particular, enzymatic sensors, including but not limited to sensors for measuring glucose and lactate, may have shortened sensor recovery times. As the sensors can recover faster, a greater throughput can be achieved.

EXEMPLIFICATION

The analyte concentration recording module 124 determines the concentration of the analyte within the sample using the calculated end point response and report the analyte concentration with a flag if the validation module 122 determines that the CV and $R^2$ are not within acceptable limits. Conversely, if the CV and $R^2$ are within acceptable limits, then the analyte concentration recording module 124 may report the concentration of the analyte without a flag. Analytes that may be measured according to the method of the invention include, but are not limited to for example, hematocrit, the ion concentration of calcium, potassium, chloride, sodium, glucose, lactate, creatinine, creatine, urea, partial pressure of O2 and/or CO2, or any other analyte for which a sensor exists. In various embodiments, the flag may be a data bit that may be represented visually as a flag, a symbol, or aurally, as a beep, a tone, or in any other manifestation that may indicate to a user that the either the CV or the $R^2$ is not within acceptable limits.

Figure 2:
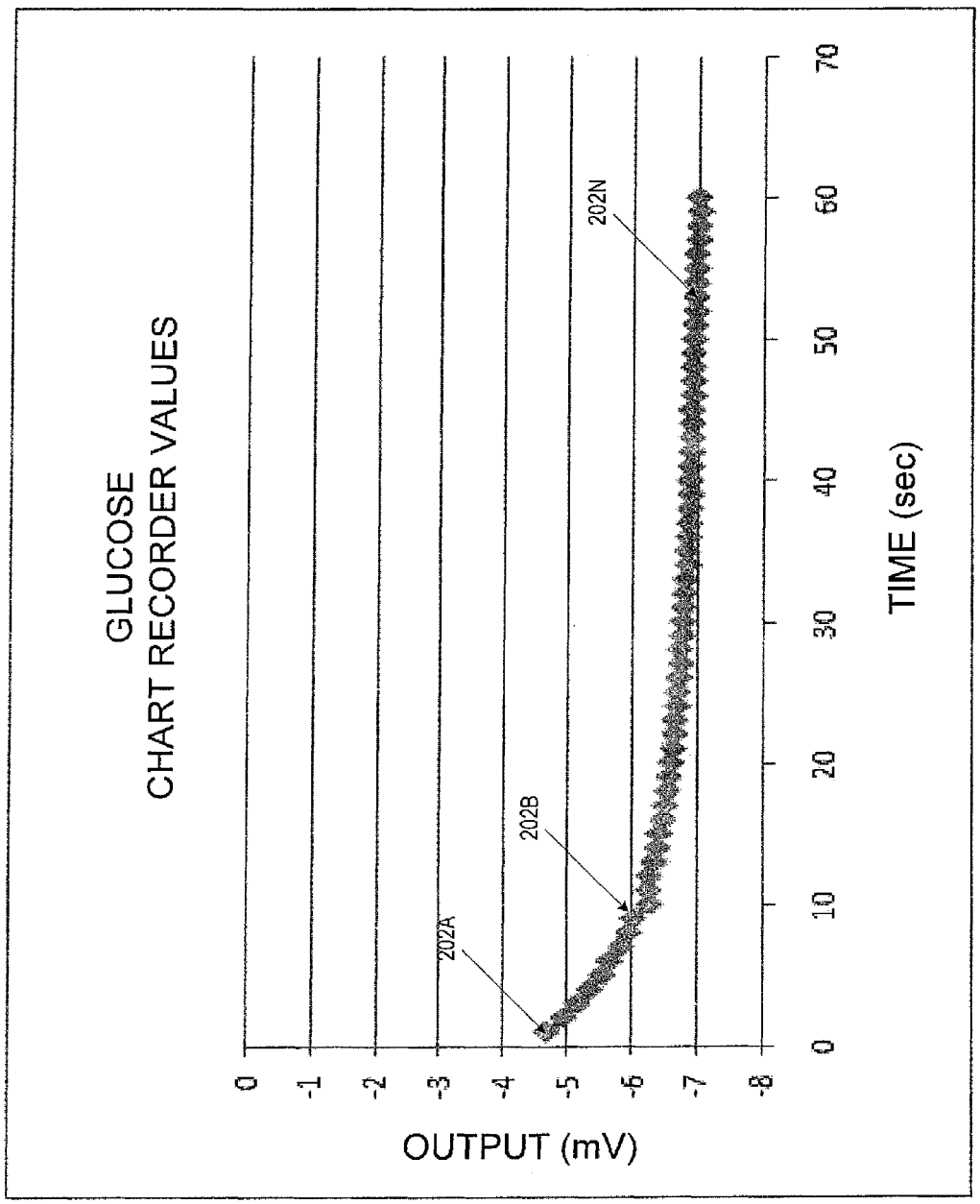
FIG. 2 shows an exemplary plot of voltage versus time for experimental data generated by a sensor for measuring the concentration of glucose according to one embodiment of the invention.

Referring now to FIG. 2, an exemplary plot of voltage versus time for experimental data generated by a sensor for measuring the concentration of glucose is shown. In particular, the plot shows a series of data points 202A-N that are captured from a data signal generated by the sensor 140. The data points indicate an output value, such as a voltage, current, or charge. In various embodiments, data points from the generated signal may be recorded over time and plotted against time. The plot shown in FIG. 2 is generated by plotting the recorded data points 202A-N against time. In the present embodiment, the data points are recorded every second. However, in various embodiments, data points may be recorded at time intervals that are less than or more than a second.

It should be appreciated that by recording data points at time intervals less than a second, more data is generated, which may allow for a more accurate plot, but may also utilize additional computing resources, which may be undesirable, depending on system resources. Alternatively, data points that are recorded at time intervals substantially exceeding a second may provide a less accurate plot. In any event, the length of the time intervals between data points is an implementation choice that may be determined based on various factors, such as the end point response time of the sensor, limitations with respect to computing resources, the nature of the sensor and analyte, and the like.

Figure 3:
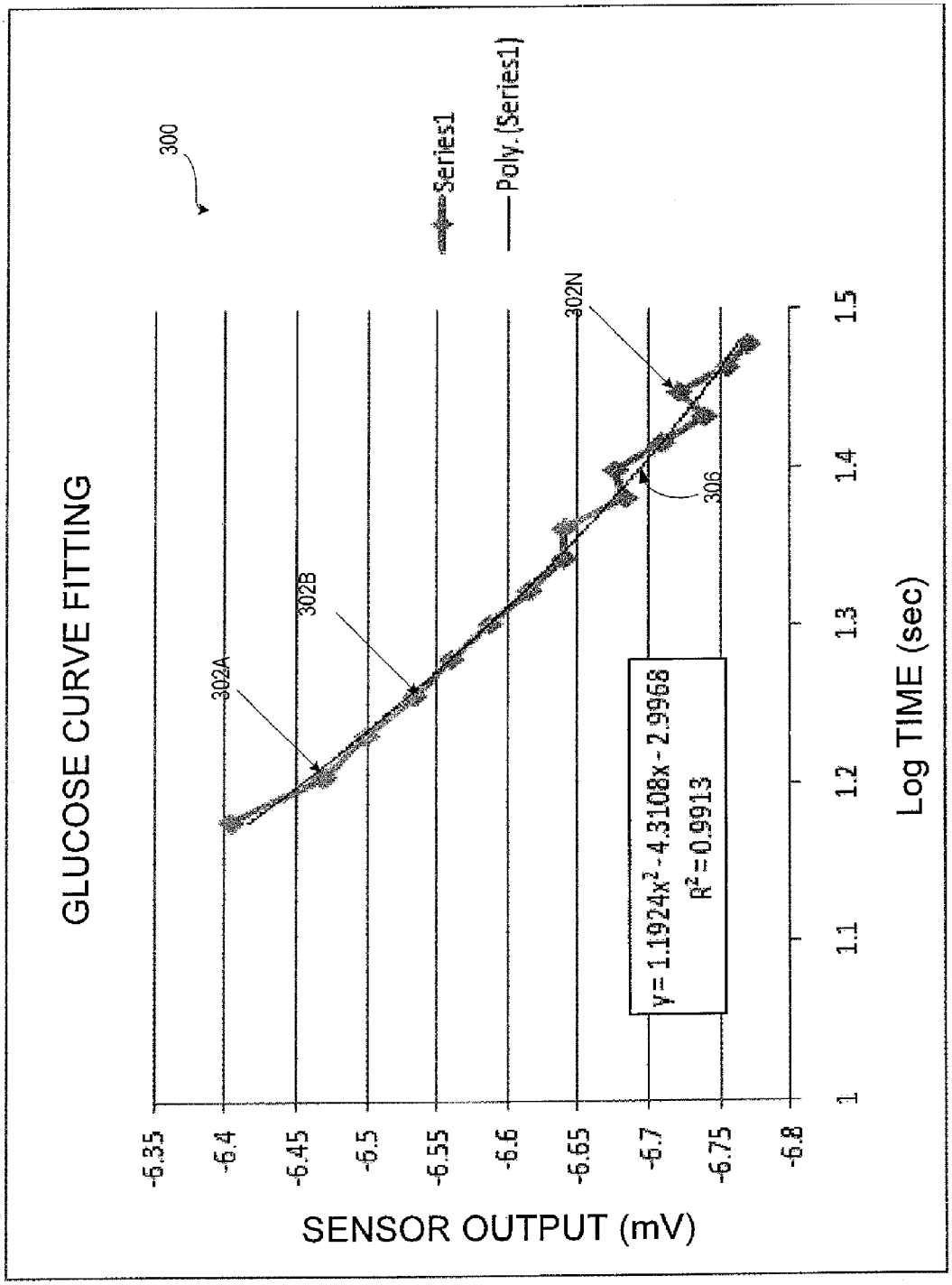
FIG. 3 shows an exemplary plot of voltage versus logarithmic function of time using a portion of the experimental data of FIG. 2 according to one embodiment of the invention.

Referring now to FIG. 3, an exemplary plot of voltage versus a logarithmic function of time using a portion of the experimental glucose data of FIG. 2 is shown. As described above, once the data points corresponding to the data signals received from the sensor are recorded, the data point selection module 114 may select pertinent data points from the recorded data points. The selected data points may then be converted to a logarithmic scale, such as base 10 or natural log. Upon converting the data points to the logarithmic scale, the converted data points 302A-N are plotted as voltage values versus logarithmic function of time.

As shown in FIG. 3, once the converted data points are plotted on the voltage versus logarithmic function of time scale, the plot 300 may be shown. This allows the curve fitting module 118 to determine a curve 306 that closely matches the converted data points 302A-N. Then, the curve fitting module 118 may determine a curve fitting equation based on the curve 306 that is simpler than existing curve fitting equations utilized in sensor technologies. Existing curve fitting equations require finding roots of non-linear equations, whereas the techniques disclosed herein do not require finding such roots. Finding roots of non-linear equations is computationally intensive, and when dealing with systems that have high throughputs, the severity of the problem becomes even more apparent. As a result, by utilizing curve fitting equations that do not require finding roots of non-linear equations, the analyte concentration measurement system 102 requires fewer computational resources than existing systems. This translates to various advantages over existing systems, including but not limited to increased throughputs, reduced costs of manufacture, and a smaller physical and energy footprint. Further, it should be appreciated that the display step may not be necessary as the curve fitting equation may be determined without having to plot data points or draw a curve that fits the data points.

According to various embodiments, the curve fitting equation may typically be a second degree logarithmic equation that has a general form of $$s(t)=a(\log(t))^2+b(\log(t))+c,$$

where a, b, and c are the polynomial coefficients that are determined based on the converted data points, and s(t) is the calculated sensor output at a particular time t. The precise values of a, b, and c. which are determined experimentally for each sensor configuration used, depend in part upon the concentration of the analyte, the size of the sample, the temperature, the geometry of the sensor transducer setup, and other parameters. Once the values of a, b, and c have been determined for a sensor configuration, the curve fitting equation may be used to rapidly estimate the concentration of the analyte in the sample. According to the invention, there is no need to wait for the sensor to provide its final reading to determine the analyte concentration.

It should be appreciated that the selection of the data points to be converted plays an important role in determining the accuracy of the curve fitting equation. Although conventional wisdom would suggest that the greater the number of data points utilized for determining the curve fit, the better.

The present invention discloses that such wisdom is not necessarily true. Rather, the range from which the data points are selected may play an even more important role. In various embodiments, the data points selected to be converted to the logarithmic function of time scale were the data points generated from 15-30 seconds after the analyte was first exposed to the sensor. In other embodiments, data points from 15-35 seconds after the analyte was first exposed to the sensor were used without significant improvements in accuracy. Similarly, data points from 10-25 seconds after the analyte was first exposed to the sensor were used but produced some results that were not accurate enough. It should be appreciated that the data points selected may vary based on the type of sensor and analyte, end point response time, amongst other factors. In various embodiments, the time range for selecting the data points may be determined through empirical methods.

As described above, the end point response value of the sensor may be calculated by solving the equation for a time that is within the equilibrium region of the sensor response curve. Once the end point analyte related value is calculated using the curve fitting equation, the end point response value is converted to a value corresponding to the concentration of the analyte, using, for example, a method comprising a calibration value (e.g. a ration, a calibration point, a difference value, etc.).

Figure 4:
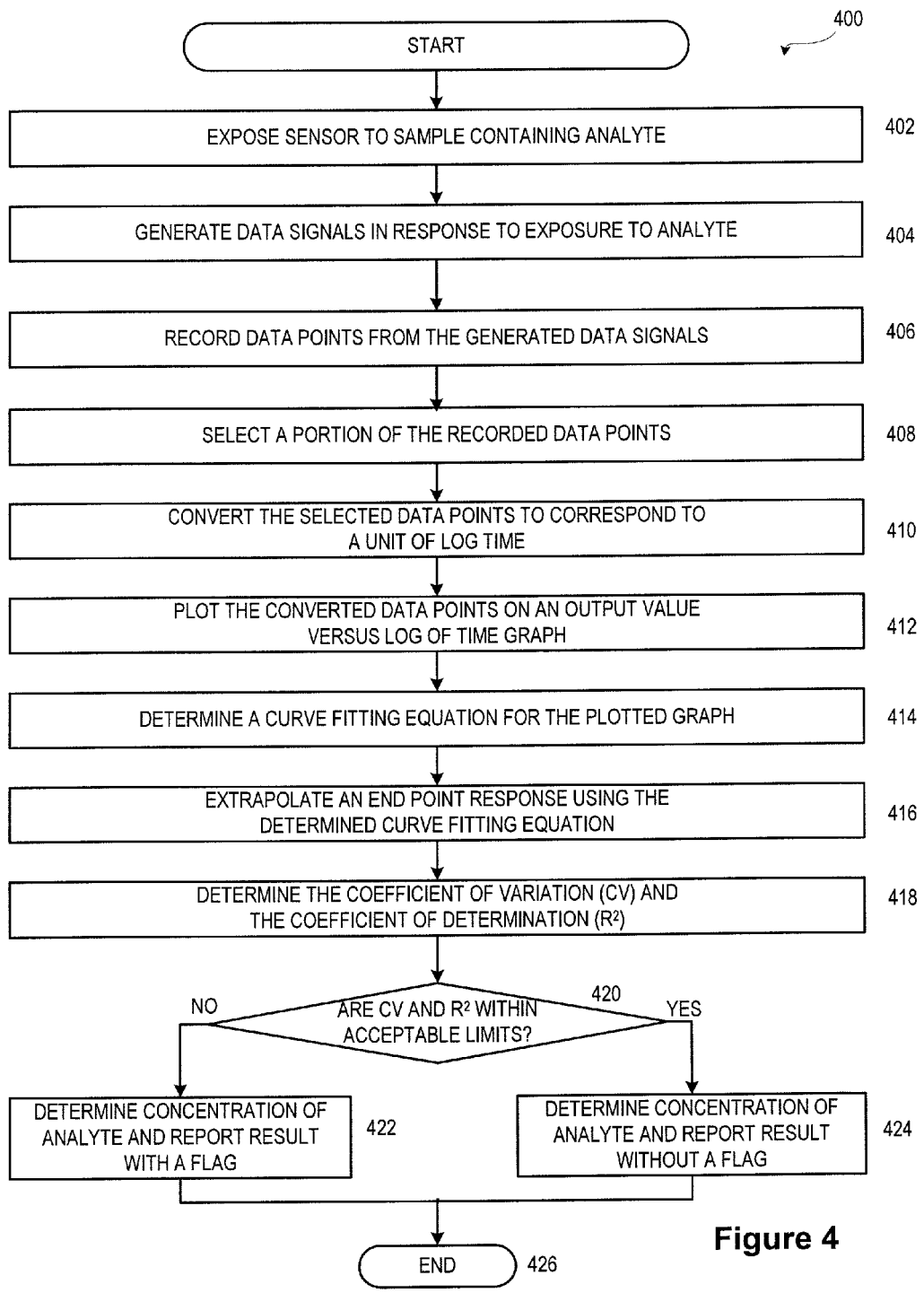
FIG. 4 is an exemplary logical flow diagram for predicting the end point response of the sensor according to one embodiment of the invention.

Referring now to FIG. 4, an exemplary logical flow diagram for estimating the concentration of an analyte within a sample is shown. A routine 400 begins at operation 402, where the sensor 140 is exposed to a sample containing the analyte. As described above, the electrochemical sensor 140 may be responsive to the levels of concentration of an analyte within the sample.

From operation 402, the routine 400 proceeds to operation 404, where the sensor 140 may generate one or more data signals in response to the exposure to the analyte. In various embodiments, the data signals may be in the form of a voltage, current, charge, or any other type of measurable output. These data signals are continuously being generated by the sensor 140 while being exposed to the analyte.

From operation 404, the routine 400 proceeds to operation 406, where the data point recording module 114 may record data points from the data signals. The granularity at which these data points are recorded may be determined by the type of sensor, the amount of analyte, the size of the sample, the temperature, amongst other factors. In one embodiment, the data signals are recorded every second. However, it should be appreciated that the frequency at which these data points are recorded may be greater than or less than one data point per second. The data points may be stored within the memory of the analyte concentration measurement system 102, or may be stored remotely at a location that is accessible by the analyte concentration measurement application 110.

From operation 406, the routine 400 proceeds to operation 408, where the data point selection module 116 may select a portion of the data points recorded by the data point recording module 114. In various embodiments, the data point selection module 116 may select data points that, when plotted, may help determine a curve that has an equation, which, when extrapolated to a time in the future, generates a result that is proximate to the actual result of the sensor 140. In various embodiments, the data point selection module 116 may select any number of data points. There is a countervailing balance that the data point selection module 116 has to consider when selecting data points. Selecting too many data points may also increase the number of outliers, which may adversely affect the accuracy of the curve being fitted, as well as selecting data points that are too far ahead in time may delay the time in which the analyte concentration measurement system 102 may determine the analyte concentration. In particular, selecting the first few data points that are recorded may cause the analyte concentration measurement system to produce inaccurate results. This is because the sensors 140, when initially exposed to the analyte, may generate noise signals, amongst other undesirable affects. Accordingly, based on empirical methods, data points selected from the kinetic region but after the initial response of the sensor 140 may generate the most accurate results, while balancing the need to determine the concentration of analyte in the shortest time, without significantly compromising on accuracy.

From operation 408, the routine 400 proceeds to operation 410, where the curve fitting module 118 converts the selected data points having an output value corresponding to a particular time to a unit of logarithmic function of time. In various embodiments, the base of the logarithmic scale may be base 10, or natural log (ln e). By doing so, a curve generated by the plotted converted data points may be more accurate and utilizes less data points than existing curve fitting equations.

From operation 410, the routine 400 proceeds to operation 412, where the curve fitting module 118 may plot the converted data points on a graph. In various embodiments, the Y-axis is an output value gathered from the data signal generated by the sensor 140, and the X-axis is a logarithmic function of time. From operation 412, the routine 400 proceeds to operation 414, where the curve fitting module 118 may determine a curve fitting equation for the plotted graph. In various embodiments, the curve fitting module 118 may determine a curve fitting equation that is a second degree logarithmic polynomial having the form $s(t)=a(\log(t))^2+b(\log(t))+c$, where a, b, and c are the polynomial coefficients that are determined based on the converted data points, and s(t) is the calculated sensor output at a particular time t. The precise values of a, b, and c. which are determined experimentally for each sensor configuration used, depend in part upon the concentration of the analyte, the size of the sample, the temperature, the geometry of the setup, and other parameters. It should be appreciated that the curve fitting module may not necessarily plot the data points to determine a curve that fits the data points. In some embodiments, the curve fitting module 118 may be able to determine a curve that fits the data points without having to plot the data points. Commercially available curve fitting software may be utilized to determine a curve and a corresponding equation that fits the selected data points.

From operation 414, the routine 400 proceeds to operation 416, where the extrapolation module 120 extrapolates the calculated end point response of the sensor 140 by solving the curve fitting equation for a time that falls within the equilibrium region. From operation 416, the routine 400 proceeds to operation 418, where the validation module 122 validates the end point response for accuracy. According to some embodiments, the validation process includes determining the coefficient of variation (CV) and the coefficient of determination ($R^2$) using the formulas of CV and $R^2$ that are presented above.

From operation 418, the routine 400 proceeds to operation 420, where the validation module determines whether the CV and the $R^2$ are within acceptable limits predefined by the analyte concentration measurement system 102. In various embodiments, these limits may allow for the CV and $R^2$ to fall within an acceptable range, which may be known by those persons having ordinary skill in the art. In one embodiment, the limits may allow for the $R^2$ to fall between 0.98 and 1. The coefficient of determination ($R^2$) indicates how well the data and the curve fit function match. The closer the value of $R^2$, the better the match.

If, at operation 420, the validation module 122 determines that either the CV, $R^2$, or both the CV and $R^2$ not within the acceptable limit, the routine 400 proceeds to operation 422, where the analyte concentration reporting module 124 determines the concentration of the analyte using the extrapolated end point response, and reports the analyte concentration with a flag indicating that the result does not fall within the acceptable limits.

However, if at operation 420, the validation module 122 determines that both the CV and $R^2$ are within the acceptable limit, the routine 400 proceeds to operation 424, where the analyte concentration reporting module 124 determines the concentration of the analyte using the extrapolated end point response, and reports the analyte concentration without a flag. From operation 422 and 424, the routine 400 ends at operation 426.

According to various embodiments, it may be desirable to provide a system for calibration of the sensors 140. A self-calibration system for measuring the analyte concentration may be used to correct for imprecisions in the manufacturing of the sensor, thus reducing the time and cost of manufacture. In addition, the self-calibration system may be used to compensate for small magnitudes of noise generated by the sensor or other components of the analyte concentration measurement system 102.

According to various embodiments, the disclosure presented herein may be utilized to reduce the time for determining an important response time of electrochemical sensors. In some embodiments, the electrochemical sensors may be used in a diffusion control response environment such as to calculate concentration levels of pO2, pCO2, glucose and lactate. In addition, the methodology may also be used for the end point detection of ion selective electrodes, such as and Na, K, Cl and Ca. However, such sensors typically exhibit fast responses and therefore an endpoint sensor response prediction may not be necessary.

What is claimed is:

1. A system for increasing sample throughput, comprising:
 a sensor configured to generate data signals in response to being exposed to an analyte within a sample;
 a processor; and,
 at least one non-transitory computer usable medium having computer readable code embodied therein, the computer readable code being executed in the processor to,
  record data points associated with the data signals,
  select a series of data points corresponding to a portion of a kinetic region time range from the recorded data points,
  convert the selected data points to a logarithmic function of time scale,
  evaluate the converted data points,
  determine a curve that fits the evaluated data points,
  determine a curve fitting equation corresponding to the curve, wherein the curve fitting equation is of the form $s(t)=a(\log(t))^2+b(\log(t))+c$, wherein t represents time, s(t) represents the data point at time t, and a, b and c are fit parameters for a second order polynomial and are determined based on the initial sensor response,
  extrapolate an end point response of the sensor using the curve fitting equation; and
  calculate, using the extrapolated end point response, a value corresponding to the analyte.

2. The system of claim 1, wherein the data points are recorded at equal time intervals.

3. The system of claim 1, wherein the kinetic region time range extends from a first time when the sensor is first exposed to the analyte to a second time when the data signals generated by the sensor are substantially similar to an actual end point response of the sensor.

4. The system of claim 3, wherein the portion of the kinetic region time range begins at approximately fifteen seconds after the sensor is exposed to the analyte.

5. The system of claim 3, wherein the portion of the kinetic region time range ends approximately thirty seconds after the sensor is exposed to the analyte.

6. The system of claim 1, wherein extrapolating an end point response of the sensor using the curve fitting equation comprises solving the curve fitting equation for a time when then the data signals generated by the sensor are substantially similar to an actual end point response of the sensor.

7. The system of claim 1, wherein the sensor is configured to have a diffusion controlled response.

8. The system of claim 1, wherein the computer readable code being executed in the processor further causes the processor to:
 determine a concentration of the analyte using the calculated end point response; and
 present the determined concentration of the analyte.

9. The system of claim 1, wherein the computer readable code being executed in the processor causes the processor to validate the calculated value corresponding to the analyte.

10. The system of claim 9 wherein, white validating the calculated end point response, the computer readable code being executed in the processor causes the processor to:
 determine a coefficient of variation;

determine a coefficient of determination; and
determine whether the determined coefficient of variation and coefficient of determination are within acceptable limits when validating said calculated end point response.

11. The system of claim 10, wherein the computer readable code being executed in the processor further causes the processor to:
determine a concentration of the analyte using the calculated end point response;
upon determining that the determined coefficient of variation and the coefficient of determination are within acceptable limits, present the determined concentration of the analyte without a flag; and,
upon determining that at least one of the determined coefficient of variation and the coefficient of determination is not within acceptable limits, present the determined concentration of the analyte with a flag.

12. The system of claim 1, wherein the computer readable code executed in the processor further causes the processor to present, as an output, the calculated value corresponding to the analyte.

13. A method for increasing sample throughput, comprising:
receiving, from a sensor, data signals generated in response to being exposed to an analyte within a sample;
recording data points associated with the data signals;
selecting a series of data points corresponding to a portion of a kinetic region time range from the recorded data points;
converting the selected data points to a logarithmic function of time scale;
plotting the converted data points;
determining a curve that fits the plotted data points;
determining a curve fitting equation corresponding to the curve, wherein the curve fitting equation is of the form $s(t)=a(\log(t))^2+b(\log(t))+c$, wherein t represents time, s(t) represents the data point at time t, and a, b and c are fit parameters for a second order polynomial and are determined based on the initial sensor response;
extrapolating an end point response of the sensor using the curve fitting equation; and
calculating, using the extrapolated end point response, a value corresponding to the analyte,
wherein the receiving, recording, selecting, converting, plotting, determining a curve, determining a curve fitting equation, extrapolating, and calculating are performed by one or more processors executing computer readable code embodied in non-transitory computer usable media.

14. The method of claim 13, wherein selecting a series of data points corresponding to a portion of a kinetic region time range from the recorded data points comprises selecting data points that correspond to a time period beginning when the sensor is first exposed to the analyte and ending when the data signals generated by the sensor are substantially similar to an actual end point response of the sensor.

15. The method of claim 13, wherein selecting a series of data points corresponding to a portion of a kinetic region time range from the recorded data points comprises selecting data points that correspond to a time period beginning at about fifteen seconds after the sensor is exposed to the analyte and ending about thirty seconds after the sensor is exposed to the analyte.

16. The method of claim 13, wherein extrapolating an end point response of the sensor using the curve fitting equation comprises solving the curve fitting equation for a time when then the data signals generated by the sensor are substantially similar to an actual end point response of the sensor.

17. The method of claim 13, further comprising;
determining a concentration of the analyte using the calculated end point response;
and,
presenting the determined concentration of the analyte.

18. The method of claim 13, further comprising:
determining a coefficient of variation;
determining a coefficient of determination; and
determining whether the determined coefficient of variation and coefficient of determination are within acceptable limits.

19. A non-transitory computer-readable storage medium having computer executable instructions stored thereon, which when executed by a computer, cause the computer to:
receive, from a sensor, data signals generated in response to being exposed to an analyte within a sample;
evaluate a curve defined by a second order quadratic equation that matches the data signals received from the sensor, wherein the curve fitting equation is of the form $s(t)=a(\log(t))^2+b(\log(t))+c$, wherein t represents time, s(t) represents the data signal at time t, and a, b and c are fit parameters for a second order polynomial and are determined based on the initial sensor response;
extrapolate an end point response of the sensor using the curve; and calculate, using the extrapolated end point response, a value corresponding to the analyte.

20. The non-transitory computer-readable storage medium of claim 19, having further computer-executable instructions stored thereon, which when executed by the computer cause the computer to:
determine a concentration of the analyte using the calculated value corresponding to the analyte; and
present the determined concentration of the analyte.

21. The non-transitory computer-readable storage medium of claim 19, having further computer-executable instructions stored thereon, which when executed by the computer cause the computer to:
validate the calculated value corresponding to the analyte by
determining a coefficient of variation;
determining a coefficient of determination; and
determining whether the determined coefficient of variation and coefficient of determination are within acceptable limits.

* * * * *